United States Patent [19]
Laurin et al.

[11] Patent Number: 5,154,186
[45] Date of Patent: Oct. 13, 1992

[54] SPINAL RESTRAINT

[76] Inventors: Frederick J. Laurin, 7 Frid Blvd., Midhurst, Ontario, Canada, L4M 4S5; Klaus K. P. Kuehn, 854 Breda Avenue, Pickering, Ontario, Canada, L1W 2K5

[21] Appl. No.: 508,384

[22] Filed: Apr. 12, 1990

[51] Int. Cl.$^5$ .......................... A61F 5/37; A61F 5/00; A61G 1/00
[52] U.S. Cl. ...................... 128/870; 602/36; 5/625
[58] Field of Search ............... 128/869, 846, 870, 872, 128/873; 5/82 R, 81; 602/32-36, 39-40

[56] References Cited

U.S. PATENT DOCUMENTS

| | | | |
|---|---|---|---|
| 2,361,328 | 10/1944 | Springer | 128/87 B |
| 3,306,287 | 2/1967 | Arp | 128/870 |
| 3,672,364 | 6/1972 | Rankin | 128/870 |
| 4,034,748 | 7/1977 | Winner | 128/870 |
| 4,252,113 | 2/1981 | Scire | 128/870 |
| 4,259,950 | 4/1981 | Klippel | 128/870 |
| 4,267,830 | 5/1981 | Vick | 128/87 B |
| 4,369,982 | 1/1983 | Hein et al. | 5/82 R |
| 4,601,075 | 7/1986 | Smith | 128/870 |
| 4,655,206 | 4/1987 | Moody | 128/870 |
| 4,899,736 | 2/1990 | Nesbitt | 128/87 B |
| 5,014,724 | 5/1991 | Miller | 128/870 |

OTHER PUBLICATIONS

Emergency Medical Services catalogue, 1988 Safety Supply Canada-pp. 6 to 10.

Primary Examiner—Michael A. Brown
Attorney, Agent, or Firm—Bereskin & Parr

[57] ABSTRACT

The present invention provides apparatus for restraining a patient having a suspected spinal injury. The apparatus is in the form of a spinal restraint comprising a rigid board, a plurality of restraining straps, a head support, a foot support, and carrying handles. The restraining straps extend laterally across the board from side portions thereof, the straps being longitudinally removable and laterally retractable. The head support is adapted for immobilizing the head of a patient and comprises a center support for supporting the back of the head of a patient and two side supports, one on each side of the central support, each one for supporting the side of the head of a patient and being movable between a support configuration and a loading and storing configuraiton in which the side support lies substantially flush with the center support. The foot support is adapted for supporting the feet of a patient and in a support configuration extends from the board, the support being movable to a storage configuration in which the support lies substantially flush with the board. The foot support is mounted on a carriage adapted for engaging a track extending longitudinally of the board, the carriage including a locking mechanism for locking the carriage, the foot support, at selected locations on the board. The handles are adapted for use in carrying the board and are located at the ends of the board, and are movable between a carrying configuration in which the handles extend beyond the ends of the board.

65 Claims, 8 Drawing Sheets

SPINAL RESTRAINT

FIELD OF THE INVENTION

This invention relates to apparatus for restraining a patient, and more particularly to a spinal restraint for use in immobilizing a patient with a spinal injury or with a suspected spinal injury.

BACKGROUND OF THE INVENTION

When a person is involved in an accident or is injured in any way and it is considered possible that the person may have sustained a spinal injury it is essential that the person be immobilized in such a way that minimal stress is placed upon the spine, such stress, typically caused by movement, possibly resulting in fatal or crippling injury. For this reason, emergency response personnel, typically ambulance crew and paramedics, carry spinal restraints in their vehicles for use in immobilizing and safely transporting a person with a suspected spinal injury.

The traditional spinal restraint is known as a fracture or spine board and is simply a planar plywood sheet provided with hand holds spaced along the side of the board. The board is typically slid beneath the patient, who is already fitted with a cervical collar, and then lateral straps are used to firmly secure the patient to the board. This form of board has the advantages of low cost and simplicity. The planar board is also very compact, which is essential due to the limited space available on ambulances and the like, and thus allows up to four boards to be carried by a single ambulance: though local regulations may vary, it is common for local health authorities to require that an ambulance carries at least two boards.

The use of this form of board requires the provision of separate restraint straps which must be separately stored and carried and which may well be mislaid and it can be difficult to secure a patient using only lateral restraint straps. Also, the provision of hand holds only on the side of the board may also present problems when a patient has to be carried through a narrow opening.

Certain spine boards are also provided with fixed foot rests, such as the Imperial Back Board with Foot Rest (Trade-mark), as supplied by Safety Supply Canada, of Richmond Hill, Ontario. A further board is disclosed in U.S. Pat. No. 4,369,982 to Hein et al, which discloses a spine board having a detachable foot support to prevent a patient from sliding off the board when it is raised from the horizontal position. The foot support assembly may be positioned in one of various positions by providing pin receiving apertures at the foot of the board for engagement with pins provided on the foot support. The patent also discloses the use of a wheel assembly which may be fixed to the spine board so that the board can be easily transported by one person.

A further variation on the basic board is disclosed in U.S. Pat. No. 4,655,206 to Moody, which describes a spinal restraint comprising a rigid board and a strap for tying the patient to the board. Various slots are provided in the edge of the board such that the strap can be laced from side to side over the patient. The restraint also includes a U-shaped head restraint pad which may be slid onto the head of the patient after the patient has been placed on the board, and which is secured to the board by clips and also by the strap which extends over shoulder engaging portions of the head restraint.

In U.S. Pat. No. 4,267,830 to Vick there is disclosed a combination spine board and head stabilizer, the head stabilizer being removably mounted on the board and being provided with head brackets swivally mounted on a head bracket support, the height and spacing of the head brackets being adjustable to suit patients of different sizes. A chin strap is also provided. Restraining straps are provided and are provided with a locking mechanism for locking the ends of the strap to the board, the strap ends including a releasable latch device for location in apertures provided at various positions on the board.

A somewhat different form of restraint is also available, in the form of a vest and head restraint which can be used to immobilize the upper body of a patient, the vest being attached to the body of the patient while the head restraint is used to immobilize the head. Such a device, known as the Tacit Cervical Immobilization Device (Trade-mark) is available from Safety Supply Canada of Richmond Hill, Ontario. A somewhat simpler restraint device with a less sophisticated head restraint is available as the LSP Miller Full Body Splint/Litter, also available from Safety Supply Canada.

Although a number of the restraints described above are adaptable to receive patients of different sizes, the adaptation is generally not a particularly simple operation; for example, in the Hein et al Spine Board, to move the foot support assembly requires the foot support to be removed from the board and repositioned in a new position, and in the Vick Combination Spine Board and Head Stabilizer, the adjustable straps must be removed from the apertures in the board and placed in the appropriately located apertures.

Also, it is preferable to provide some traction for the patient to minimize compression stress on the possibly damaged spine. The only device in which this is addressed is the Tacit Cervical Immobilization Device in which the head restraint is moveable relative to the body vest. However, it would appear that adjustment of the device would be quite difficult.

SUMMARY OF THE INVENTION

In accordance with a first embodiment of the present invention there is provided apparatus for restraining a patient comprising a rigid board and a plurality of restraining straps for extending laterally across the board from side portions thereof to secure a patient to the board. At least one of the straps is longitudinally adjustable to accommodate patients of different sizes.

Preferably, three adjustable straps are provided and may be located on the board such that they are adapted to extend across the chest, pelvic area and upper legs of a patient.

According to a further aspect of the present invention there is provided apparatus for restraining a patient comprising a rigid board and a plurality of retaining straps for extending laterally across the board from side portions thereof to secure a patient to the board. At least one of the straps is longitudinally adjustable and is laterally retractable to accommodate patients of different sizes.

Preferably, biasing are provided to retract the strap which thus tightly engages a patient on the board.

According to another aspect of the present invention there is provided apparatus for restraining a patient comprising a rigid board and a plurality of retaining straps for extending laterally across the board from side portions thereof to secure a patient to the board. At least one of the straps is laterally retractable to accommodate patients of different sizes.

According to a still further aspect of the present invention there is provided apparatus for restraining a patient comprising a rigid board and a head support for immobilizing the head of a patient on the board. The head support comprises a centre support for supporting the back of the head of a patient and two side supports, one on each side of the central support, each one for supporting a side of the head of a patient. The side supports are moveable between a support configuration and a loading and storage configuration in which the side supports lie substantially flush with the centre support.

To position a patient on the board, the side supports are positioned in the loading and storage configuration such that the board may be slid beneath the patient. The side supports are then moved to the configuration. In the loading and storage configuration the side supports do not add to the thickness of the board and thus facilitate storage of the board.

According to a still further aspect of the present invention there is provided apparatus for restraining a patient comprising a rigid board, retaining means for securing a patient to the board, and a foot support for supporting the feet of a patient. The foot support is mounted on a carriage adapted for engaging a track extending longitudinally of the board, the carriage including a locking mechanism for locking the carriage, and the foot support, at selected locations on the board to accommodate patients of different sizes.

By securing the feet of a patient to the foot support and securing the upper body of a patient using the body retaining means, it is possible to apply traction to the spine of the patient.

According to yet further aspects of the present invention there is provided apparatus for restraining a patient comprising a rigid board, retaining means for securing a patient to the board, and handles for use in carrying the board. The handles are located at ends of the board and are moveable between a carrying configuration in which the handles extend beyond the ends of the board, and a storage configuration in which the handles are located substantially adjacent the ends of the board.

The location of the handles at the ends of the board permit bearers to carry the board from the ends and the provision of a storage configuration for the handle means allows the handles to facilitate storage of the board.

According to another embodiment of the present invention there is provided apparatus for restraining a patient comprising a rigid board, a plurality of retaining straps, a head support, a foot support, and carrying handles. The retaining straps extend laterally across the board from side portions thereof, the straps being longitudinally movable and laterally retractable. The head support is adapted for immobilizing the head of a patient on the board and comprises a centre support for supporting the back of the head of a patient and two side supports, one on each side of the central support, each one for supporting the side of the head of the patient and being moveable between a support configuration and a loading and storage configuration in which the side supports lie substantially flush with the centre support. The foot support is adapted for supporting the feet of a patient and in a support configuration extends from the board, the support being movable to a storage configuration in which the support lies substantially flush with the board. The foot support is mounted on a carriage adapted for engaging a track extending longitudinally of the board, the carriage including a locking mechanism for locking the carriage, and the foot support, at selected locations on the board. The handles are adapted for use in carrying the board and are located at the ends of the board, being moveable between a carrying configuration in which the handles extend beyond the ends of the board, and a storage configuration in which the handles are located substantially adjacent the ends of the board.

BRIEF DESCRIPTION OF THE DRAWINGS

These and other aspects of the present invention will now be described, by way of example, with reference to the accompanying drawings in which.

DETAILED DESCRIPTION OF THE DRAWINGS

Figures 1, 2, 3:
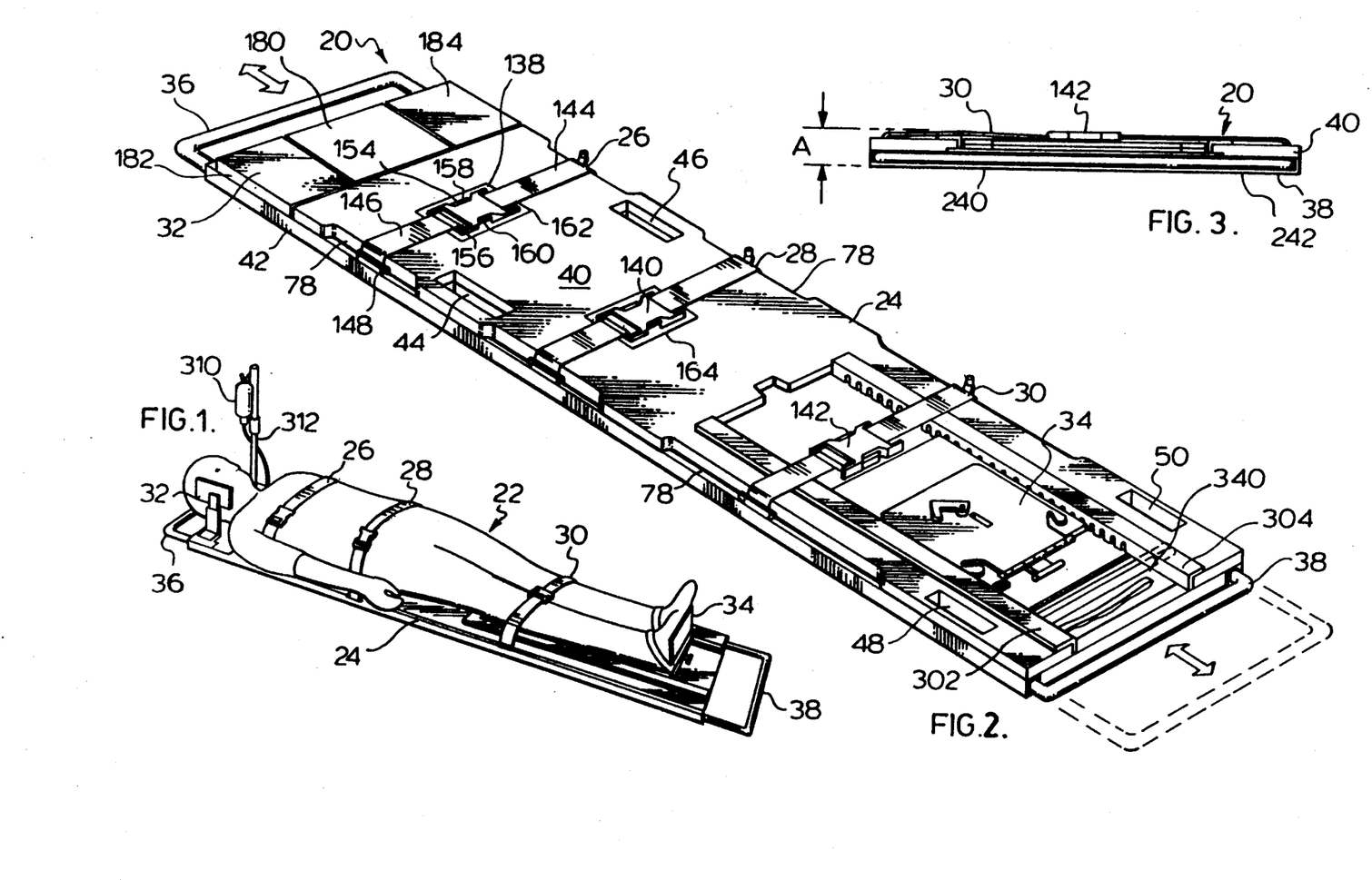
FIG. 1 is a perspective view of a patient immobilized on a spinal restraint in accordance with a preferred embodiment of the present invention.
FIG. 2 is an enlarged perspective view of the spinal restraint of FIG. 1, showing the restraint in the storage configuration.
FIG. 3 is an end view of the spinal restraint of FIG. 1 in the storage configuration.

Reference is first made to FIG. 1 of the drawings, which illustrates apparatus for restraining a patient with a suspected spinal injury. The apparatus is in the form of a spinal restraint, generally indicated at 20 on which a patient 22 is immobilized. It is the intention of the restraint 20 to restrain the patient 22 in such a way that minimal stress is placed upon the spine as any stress on or movement of an injured spine may result in fatal or crippling injury. The main components of the restraint 20 are a rigid board 24, retaining straps 26, 28 and 30 for extending laterally across the board 24 for securing the patient 22 to the board 24, a head support 32 for immobilizing the head of the patient 22, a foot support 34 for immobilizing the feet of the patient 22 and also for applying traction to the spine of the patient, and retractable carrying handles 36, 38 located at the ends of the board 24.

As will be described, the various features of the restraint 20 are arranged such that the restraint 20, when not in use, may be configured for compact storage, the storage configuration being illustrated in FIG. 2 of the drawings. This feature of the invention is particularly useful when the restraint 20 is carried by an emergency vehicle, such as an ambulance, where the storage space available on the vehicle may be severely limited. FIG. 3 of the drawings is an end view of the restraint 20 in the storage configuration and illustrates the depth A of the restraint (typically around 2″).

In the particular example of restraint illustrated in the drawings, the board 24 comprises a plywood top sheet 40 mounted on a square section aluminum alloy extrusion frame 42. This is of course just one example of board composition, and other materials, such as fibre glass and plastics could be used with equal utility. To allow proper examination of the patient while on the board, it is also desirable that the board material is x-ray transparent. In this example, four side handles 44, 46, 48, 50 are provided in the board 24 in addition to the carrying handles 36, 38 at the ends of the board 24.

Figures 4, 5, 6:
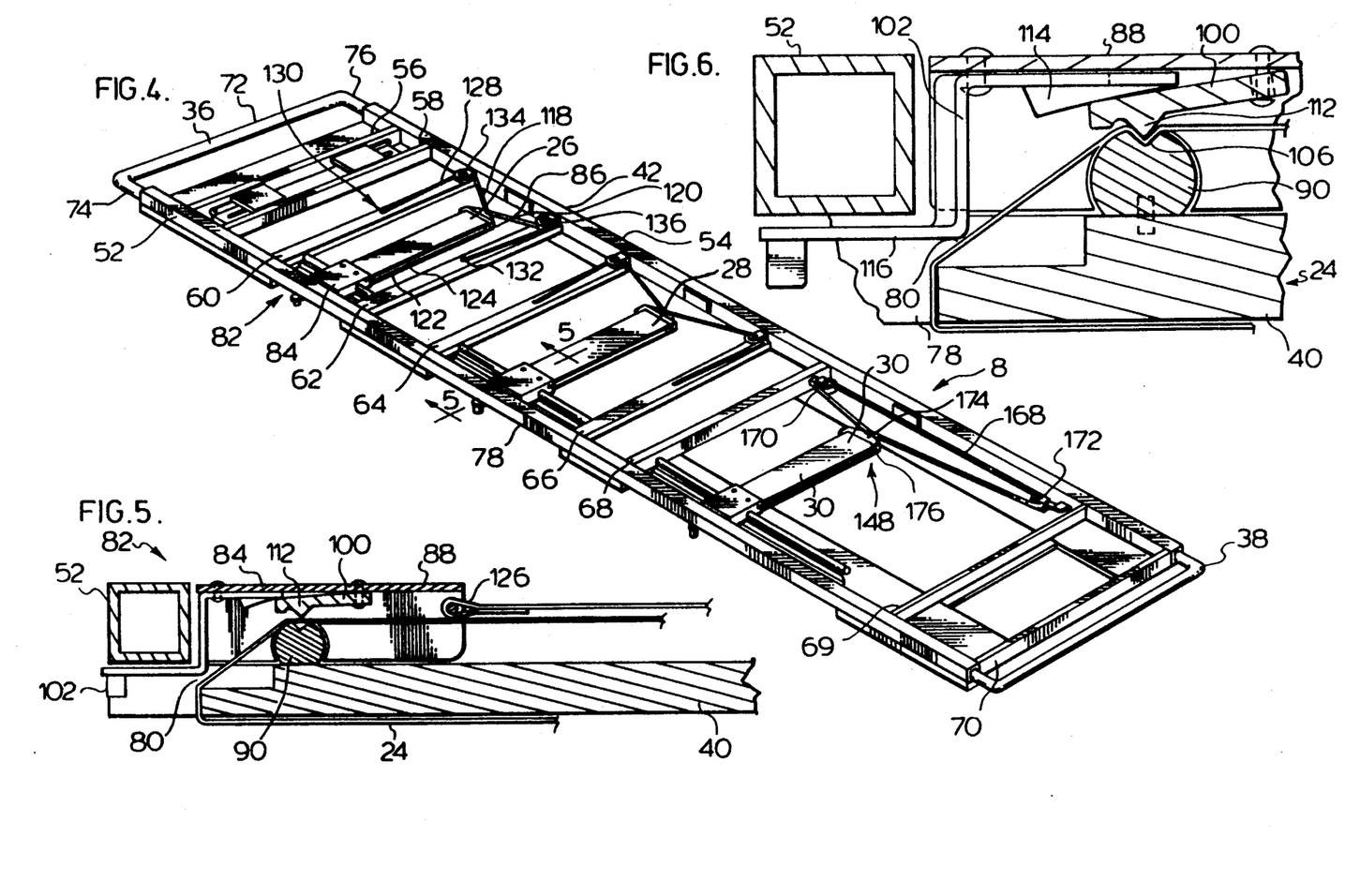
FIG. 4 is a perspective view from below of the spinal restraint of FIG. 1, with a rear cover of the restraint removed.
FIG. 5 is an enlarged scrap sectional view on lines 5—5 of FIG. 4 and showing strap locking means.
FIG. 6 is an enlarged scrap sectional view on line 5—5 of FIG. 4 and showing the locking means in the unlocked configuration.

As may be seen from FIG. 4 of the drawings, which shows the base of the restraints with a bottom cover removed, the frame 42 comprises two main side members 52, 54 and various cross members 56, 58, 60, 62, 64, 66, 68, 69 and 70. The ends of the side members 52, 54 are open to receive the carrying handles 36, 38 each of which is generally U-shaped having a cross member 72 and two side members 74, 76 which are slidably received by the side members 52, 54 of the frame. Thus the carrying handles 36, 38 may be easily moved from a storage configuration, as shown in solid outline in the bottom right hand corner of FIG. 2, to a carrying configuration, as illustrated in chain-dotted outline in the bottom right hand corner of FIG. 2. Thus the carrying handle configuration permits the restraint 20 to be carried by bearers located at the ends of the restraint 20, while not adding length to the restraint and making storage more difficult.

As may be seen from FIG. 1 of the drawings, the retaining straps 26, 28, 30 are longitudinally spaced on the board 24, one strap 26 being located on the chest of the patient, the second strap 28 being located over the pelvic area of the patient, and the third strap 30 being positioned at the upper legs of the patient. In order to accommodate patients of different sizes the straps are longitudinally adjustable and are also laterally retractable. As may be seen from FIG. 2 of the drawings, the side of the board 24 is provided with various indents 78 from which the straps 26, 28, 30 extend, the indent 78 indicating the range of longitudinal movement possible for each of the straps.

Figure 7:
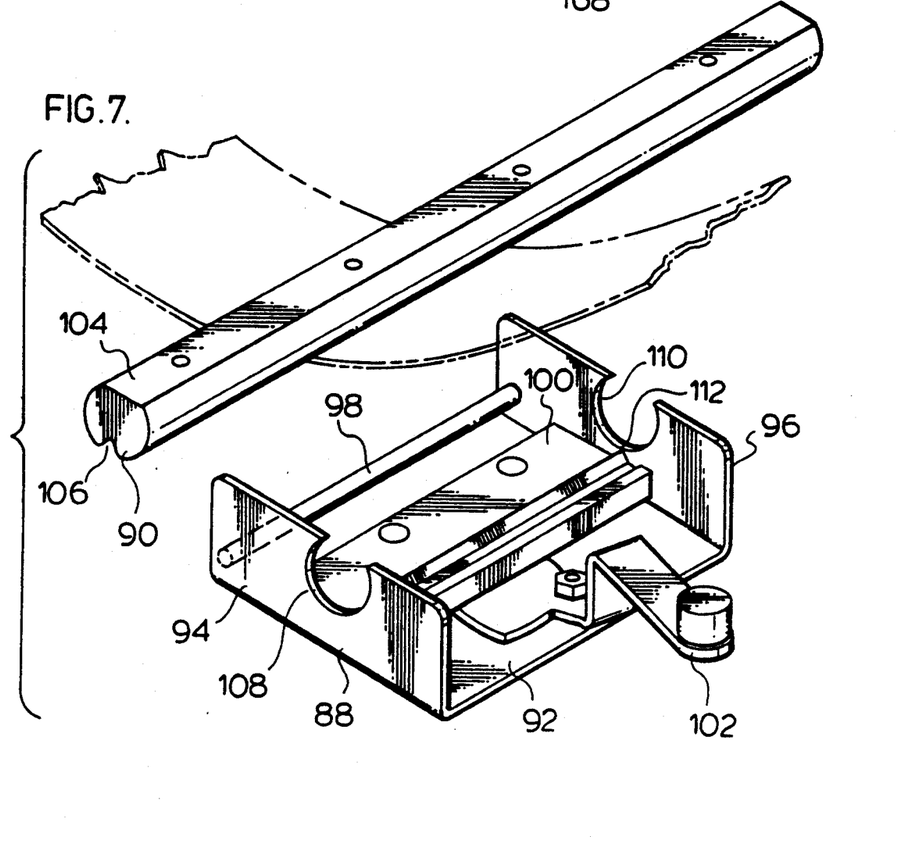
FIG. 7 is an exploded perspective view from above of the locking means and track means illustrated in FIG. 5 and 6.

The longitudinal adjustment and lateral retractability of the straps is accomplished by means provided on the underside of the board, which is shown in FIG. 4 of the drawings. The mounting of the three straps 26, 28, 30 is substantially similar, such that the mounting for the chest strap 26 will be described as being exemplary of the straps. From the upper side of the board 24, one end of the strap 26 passes through a space 80 (FIG. 5) between the side of the board 24 and side member 52 of the frame 42 to a strap locating mechanism 82 comprising a locking means 84 and a resilient strap retraction means 86. The locking means 84 is in the form of a locking buckle 88 mounted on a longitudinally extending track 90. The buckle 88 and track 90 are shown in greater detail in FIGS. 5, 6 and 7 of the drawings. The buckle 88 has a central portion 92 (FIG. 7) and two side portions 94, 96, a strap mounting rod 98 extending between the side portions 94, 96, a locking plate 100 pivotally mounted on the central portion 92 and an operating member 102 also pivotally mounted on the central portion 92. The track 90 is in the form of a part circular rod having a flattened mounting surface 104 on the upper side thereof, and a longitudinal channel 106 provided on the under side thereof. The side portions 94, 96 are each provided with an undercut slot 108, 110 for retaining the buckle 88 on the track in sliding relationship therewith. The strap 26 passes between the locking plate 100 and the lower side of the track 90 and in the unlocked configuration, as shown in FIG. 5, the strap may pass between the locking plate 100 and the track 90 and the locking buckle 88 is free to slide on the track 90.

The locking plate 100 is pivotally mounted to the central portion 92 about a longitudinal axis such that the other end of the locking plate, which is provided with a locking protrusion 112, is movable between the unlocked configuration, as shown in FIG. 5, and the locked configuration, as shown in FIG. 6, in which the protrusion engages the strap and pushes it into the channel 106 in the track. The protrusion 112 is of complimentary shape to the channel 106 such that the strap is engaged over a relatively large surface area and thus securely held in position. Also, moving the locking plate 100 to the locking configuration pushes the locking buckle 88 downwardly such that the undercut slots 108, 110 engage the track 90 and lock the buckle, and thus also the strap 26, longitudinally relative to the board.

Movement of the locking plate 100 between the locked and unlocked configurations is achieved by use of the operating member 102 which is pivotally mounted to the central portion 92 of the buckle about a vertical axis. As may be seen from FIGS. 5 and 6, the operating member 102 has a stepped profile and has an operating portion 114 in the form of a helical cam way and a handle portion 116 which is located in the indent 78 in the board 24, above the side member 52 of the frame 42. Thus, an operator may move the operating member 102, using the handle portion 116 to lock and unlock the buckle.

From the buckle 88, the strap 26 extends to a pulley 118 (FIG. 4) located on a bight 120 formed on the strap, the strap thus defining upper and lower reaches 122, 124, the lower reach extending to the strap mounting rod 98 on the buckle 88 to which the end of the strap is secured, by means of a fixed loop 126 (FIG. 5). The pulley is further mounted on a resilient elongate member in the form of a "bungee" cord 128, which is arranged to pull the pulley 118 towards the side of the board 24. The cord 128 defines a U-shape, the ends of the cord 130, 132 being fixed to the cross members 60, 62 and passing around pulley wheels 134, 136 mounted on the side member 54. Thus it may be seen that the cord 128 will tend to pull the pulley 118 towards the side member 54 to increase the length of the reaches 122, 124 and thus pull the strap through the gap 80 and retract the strap 26.

Figure 8:
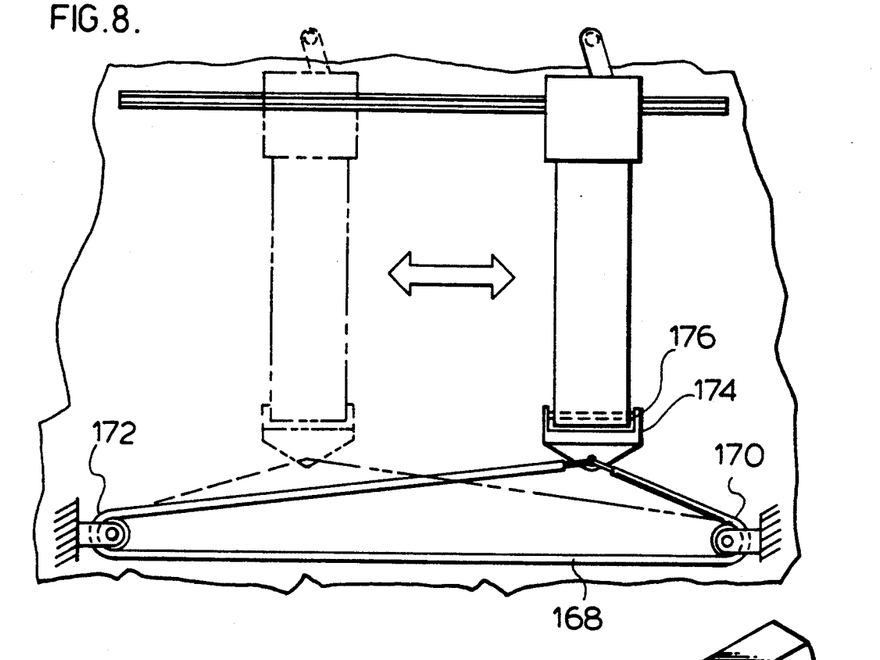
FIG. 8 is an enlarged scrap below plan view of the strap restraining means of area 8 of FIG. 4.

It will be noted from FIG. 4 and also from FIG. 8 of the drawings, that the resilient elongate member of the strap retraction means 148 of the third strap 30 is in the form of a loop 168 passing between two longitudinally spaced pulley wheels 170, 172. The strap pulley 174 is mounted on a bight 176 of the loop 166.

Figure 9:
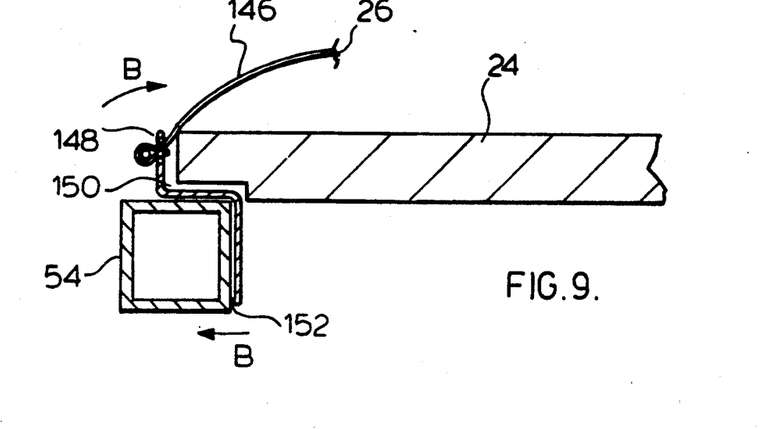
FIG. 9 is a sectional view on line 9—9 of FIG. 10.

If reference is made again to FIGS. 1 and 2 it will be noted that each strap 26, 28, 30 is provided with a releasable buckle 138, 140, 142. Again, reference will be made in particular to the buckle 138 provided on the first strap 26 to describe operation and use of the buckle 138. The buckle 138 may be separated to divide the strap 26 into two parts 144, 146. The first part 144 extends around a first side of the board 24 to the locking means 84 and resilient strap retracting means 86 as described above, while the second part 146 extends to the other side of the board 24 to a strap attachment member 148 located in an indent 78. Details of the strap attachment member may be seen in FIG. 9 of the drawings, the member 148 having a stepped profile, the strap 26 being fixed to an upper end of the member and the lower portion of the member 148 extending through a gap 150 provided between the board 24 and the side member 54 of the frame 42. When the strap 26 is loose the member 148 may slide longitudinally in the gap, and will normally be positioned such that the strap 26 extends laterally across the board 24. When the strap 26 is tightened, the member 148 is rotated in direction B such that a lower end of the member 148 is pulled into contact with the side member 54, teeth being formed in the lower end of the member by lancing the member, the teeth 152 firmly engaging the side member 54.

In use, a patient is positioned on the board 24 and the straps, with the parts 144, 146 separated, are positioned to suit the patient The buckles 138, 140, 142 are then secured, the resilient strap retraction means 86 pulling the straps 26, 28, 30 tight across the body of the patient 22. The locking buckle 88 is then locked in position such that the straps 26, 28, 30 are longitudinally and laterally fixed. Further tightening of the straps 26, 28, 30 may be achieved by pulling on an end of the strap at the buckle 138, 140, 142.

The straps illustrated are of the type having male and female parts 154, 156, the male part 154 including outwardly biased locking portions 158, 160 for locking engagement with the female part 156. To release the buckle, the locking portions 158, 160 are pressed inwardly to disengage the female part 156. It is preferred that the buckles used are secure and are not readily releasable by the patient 22; instances have been known of unsupervised patients releasing themselves from spinal restraints 20 and then moving and incurring injury.

In the storage configuration, the straps 26, 28, 30 are pulled tight across the board 24. Further, rectangular recesses 162, 164 are provided in the board 24 to permit the buckles 138, 140 to lie substantially flush with the board surface.

Figure 10:
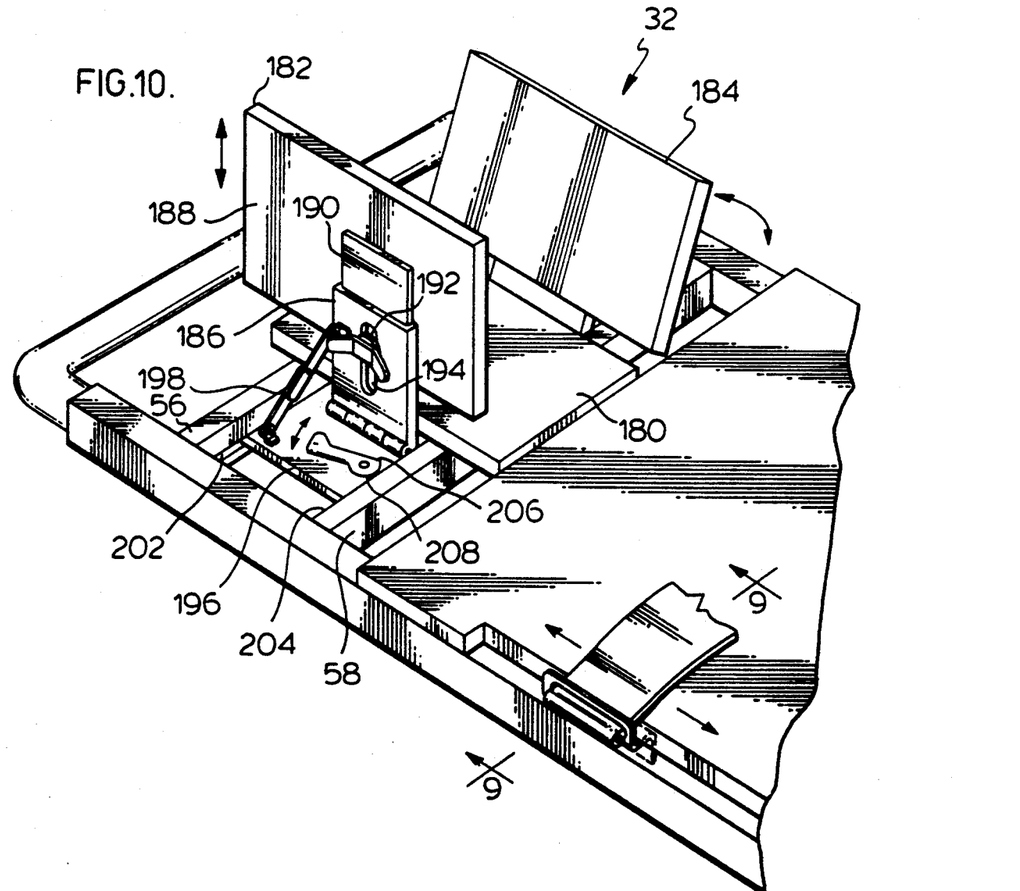
FIG. 10 is a perspective view from above of the head support portion of the spinal restraint of FIG. 1.
Figure 11:
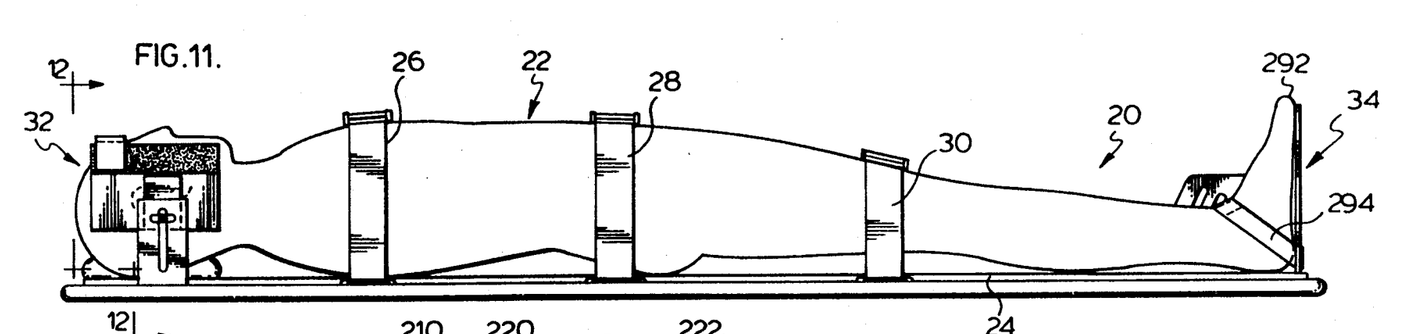
FIG. 11 is a side elevation of a patient immobilized on the spinal restraint of FIG. 1.
Figure 12:
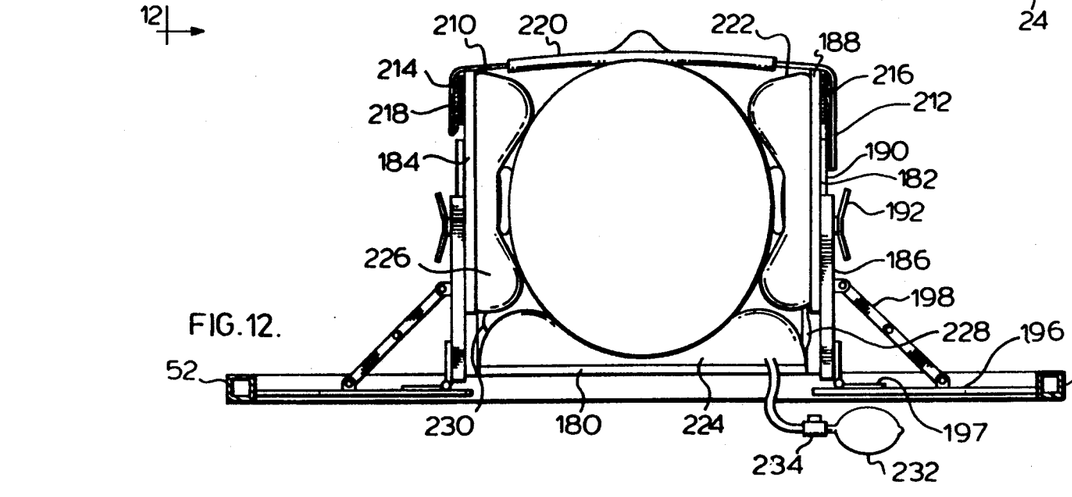
FIG. 12 is a sectional view on line 12—12 of FIG. 11.

Reference is now also made to FIGS. 10, 11 and 12 of the drawings which illustrate features of the head support 32. As may be seen from FIGS. 1 and 2 of the drawings, the head support 32 is moveable between a support configuration, as shown in FIG. 1, and a loading and storage configuration as shown in FIG. 2. The head support comprises a centre support 180 for supporting the back of a head of a patient and two side supports 182, 184 for supporting a side of a head of a patient. The centre support 180 is fixed to the board 24 and the side supports 182, 184 are moveable between a support configuration and a loading and storage configuration, FIG. 10 illustrating one of the side supports 182 in the support configuration, and the other side support 184 between configurations. From FIG. 2 it will be noted that, in the storage configuration, the side supports 182, 184 lie substantially flush with the centre support 180 and the board surface. Thus, the board may be slid beneath a patient, who may already be fitted with a cervical collar, and the side supports 182, 184 then moved to the support position once the patient has been positioned on the board.

The supports 180, 182, 184 are formed of substantially planar, rectangular boards. Each side support 182, 184 further comprises a mounting member 186 and a support member 188 in the form of a substanially planar, rectangular board. Each mounting member 186 is in the form of a shallow U to define a track extending perpendicularly of the longitudinal axis of the board, the support member 188 being provided with a complementary track engaging portion 190. The mounting member 186 and the track engaging portion 190 of the support member are arranged to permit up and down movement of the support member 188 in the support configuration. To retain the support member 188 on the mounting member 186 a screw clamp 192 extends from the track engaging portion 190 through a slot 194 in the support member 188 and may be tightened against the mounting member 186 to lock the support member 188 relative to the mounting member 186.

The mounting member 186 is pivotally mounted to a carriage member 196 on an axis parallel to the longitudinal axis of the board. A pivoted link 198 extends between the carriage member 196 and the mounting member 186 and is arranged to lock in an over centre position in the support configuration, as may be seen in FIG. 12 of the drawings. FIG. 12 also illustrates the hinge link 197 between the mounting member 186 and the carriage member 196 which is in the form of a planar rectangular plate and is located in a track formed by opposing channels 202, 204 (FIG. 10) formed in the cross members 56, 58 of the frame 42 such that the carriage member 196 and the side support may be moved laterally relative to the centre support 180. A locking lever 206 is pivotally mounted on the carriage member 196 and includes a cam portion 208 which may be brought into contact with the cross member 58.

FIGS. 11 and 12 illustrate a patient on the board with the head support 32 being used to immobilize the head of the patient. To further secure the patient a lateral strap 210 is positioned over the forehead of the patient, the ends of the straps being provided with a loop arrangement 212, 214 for engaging a corresponding hook arrangement 216, 218 provided along the upper edges of the side supports 182, 184. As may be seen in FIG. 12, a removable sleeve 220 is provided on the strap 210.

In addition to serving as an additional retaining means as described above, the strap 210 may also be used to retain the side supports 182, 184 in the loading and storage configuration, by extending the strap across the back of the restraint.

As may be seen in FIG. 12, the centre and side supports 180, 182, 184 are provided with inflatable air cushions which may be inflated to comfortably and securely locate the head of the patient in the head support 32. In the illustrated example, the cushions 222, 224, 226 are linked by lengths of tubing 228, 230 and are inflated from a bulb pump 232. To prevent the cushions 222, 224, 226 being over-inflated, the pump 232 is provided with a release valve 234, which opens when the pressure in the cushions has reached a pre-determined level.

As mentioned above, the configuration of the side supports 182, 184 facilitates loading of a patient onto the board. Also, the side supports 182, 184 are independently movable and this may be useful when, for example, the patient has a suspected head injury and a physician wishes to examine the ear of a patient; one of the side supports 182 may be lowered, the other support 184 still providing support for the head. Alternatively, the supports 182, 184 could be configured to include an ear access opening.

Figure 13:
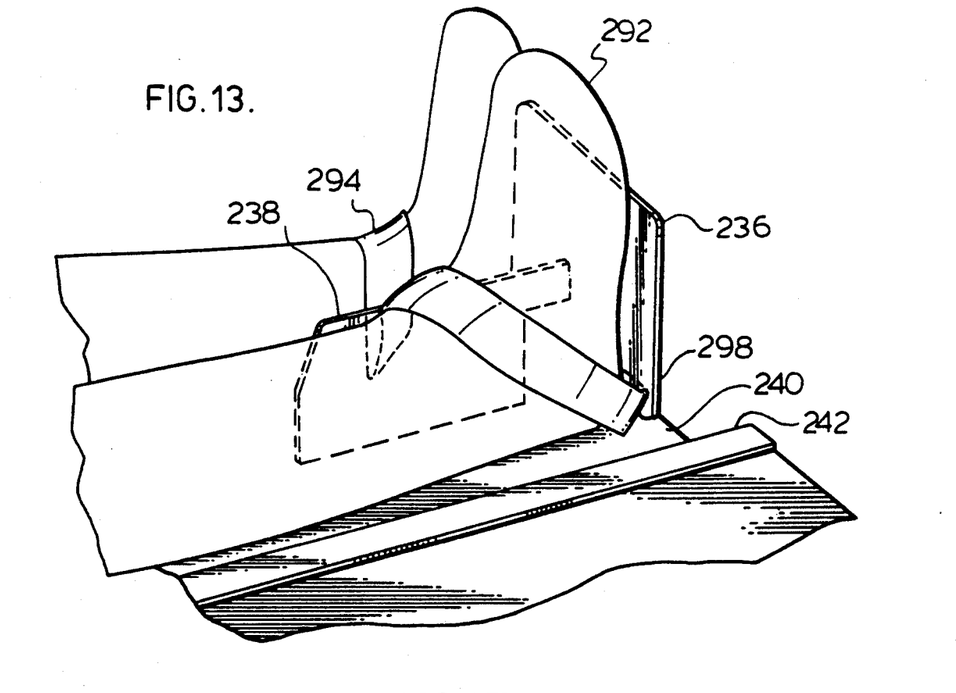
FIG. 13 is a scrap perspective view from above of the foot support of the spinal restraint of FIG. 1, and showing the feet of a patient secured to the foot support.
Figure 14:
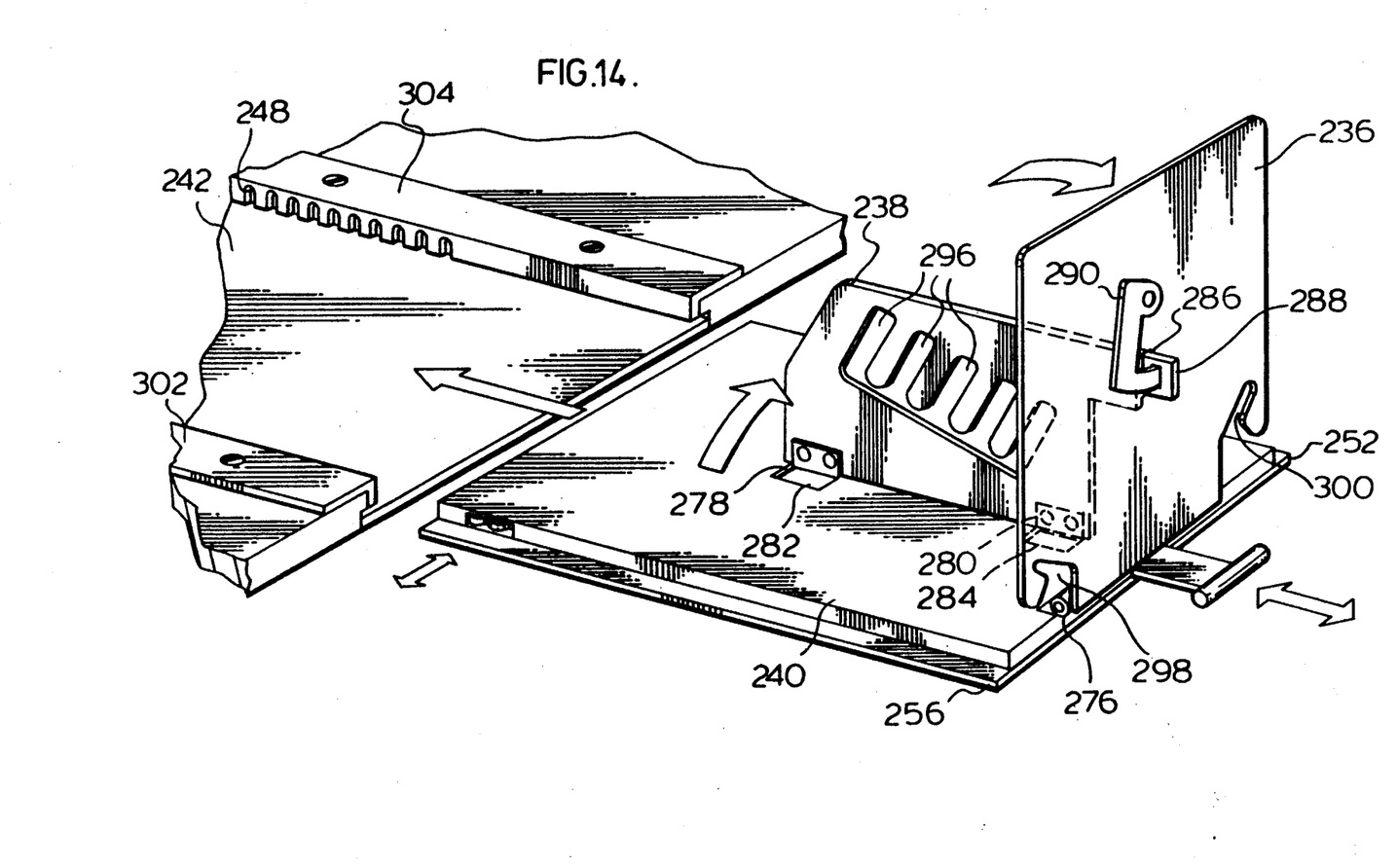
FIG. 14 is a scrap perspective view of the foot support of FIG. 13, showing elements of the foot support separated from one another.
Figure 15:
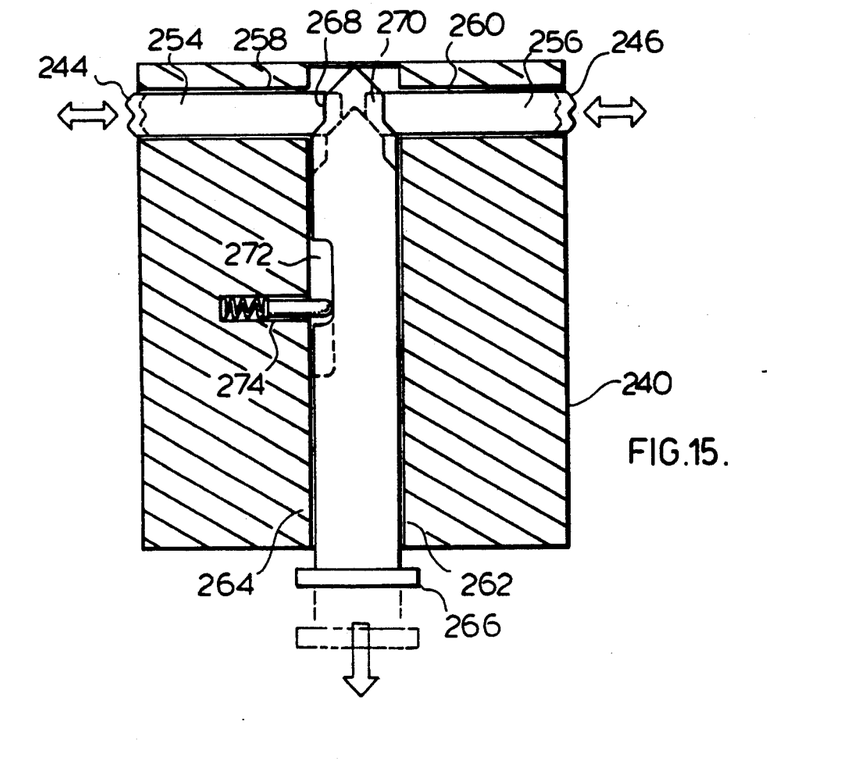
FIG. 15 is a sectional view of a portion of the foot support means illustrating a locking arrangement of the foot support means (on same sheet as FIG. 13)

References now also made to FIGS. 13, 14 and 15 of the drawings which show details of the foot support 34 which is intended immobilize the feet of a patient and also to apply traction to the spine of the patient.

The foot support 34 comprises first and second foot support members in the form of a lateral foot plate 236 for abutting the soles of the feet and a longitudinal foot plate 238 for location between the feet. The plates 236, 238 are mounted on a carriage member 240 which is received in a track in the form of a shallow trough 242 at the foot end of the board 24.

The carriage member 240 is generally rectangular and is provided with retractable locking teeth 244, 246 for engaging the sides of the trough 242 which are provided with a series of corresponding recesses 248. As may be seen from FIG. 14, the sides of the trough 242 are undercut and a corresponding flange 250, 252 is provided at the base of the carriage member 242 to be received by the sides of the trough. FIG. 15 is a sectional view through the carriage member 240 and illustrates the operation of the locking teeth 244, 246. It may be seen that the teeth 244, 246 are provided on the ends of lateral locking members 254, 256 located in corresponding laterally extending channels 258, 260. Movement of the locking members 254, 256 between the locked and unlocked positions (shown in chain-dotted outline) is achieved by use of a operating member 262 slidably located in a corresponding longitudinal channel 264. A grip portion 266 is provided at the end of the member 262 which extends from the carriage member 240, and the other end of the member 262 is provided with cam surfaces 268, 270 for engaging in end portions of the locking members 254, 256. The surfaces 268, 270 are arranged such that, in the locked configuration, the contact surfaces between the operating member 262 and the locking members 254, 256 are perpendicular to the direction of movement of the operating member 262, such that there is no tendancy for the locking members 254, 256 to push the operating member 262 towards the unlocked position.

To prevent the operating member 262 being withdrawn from the carriage member 240, one side of the member 262 is provided with an indent 272 which co-operates with a spring biased locking pin 274 which is laterally moveable relative to the member 262. The indent 272 is of sufficient length to permit the operating member 262 to be moved only between the locked and unlocked positions.

The foot plates 236, 238 are mounted on an upper surface of the carriage member 240 and are mounted to the member 240 by means of hinges 276, 278, 280 which permit the plates 236, 238 to be moved between a support configuration, as seen in FIG. 14, to a storage configuration, as may be seen in FIG. 2. It will be noted that in the storage configuration that the plates 236, 238 lie flush with or below the surface of the board. The mounting hinge 276 for the lateral foot plate 236 is arranged such that the plate is pivotable about a lateral axis and the mounting hinges 278, 280 for the longitudinal foot plate 238 are arranged such that the plate 238 is pivotable on a longitudinal axis. It will also be noted from FIG. 14 that the upper surface of the carriage member 240 includes recesses 282, 284 to accommodate the hinges 278, 280 when the foot plate 238 is in the storage configuration.

In this particular example, the lateral foot plate 236 is provided with centrally located opening 286 for receiving a projection 288 provided at the base of the longitudinal foot plate 238, a latch 290 being pivotally mounted on the lateral foot plate 236 for engaging an opening in the projection 288 and thus locking in the plates 236, 238 in the support configuration.

FIGS. 11 and 13 show the feet 292 of a patient in the foot support 234 with a restraining strap 294 securing the feet in place. The ends of the strap (not shown) are provided with some form of attachment, preferably a hook and loop tape arrangement such that the ends of the strap 294 may be easily fastened together. The strap 294 is positioned in one of a series of slots 296 (FIG. 14) provided in the longitudinal foot plate 238, and from there passes over the feet and around the base of the lateral foot plate 236. To retain the strap 294 at the base of the foot plate 236, angled slots 298, 300 are provided.

In the illustrated example, the slots 296 provided in the longitudinal foot plate 238 are formed as a comb type arrangement. In other embodiments, discrete slots could be provided. Also, the illustrated example illustrates trough sides 302, 304 formed of aluminum alloy and secured to the board. It will be noted that the upper portion of the sides extends above the surface of the board In other embodiments separate sidewalls may not be necessary and the recesses 248 could be formed integrally with the board material.

The arrangement of the carriage member 240 is such that, once the feet of a patient are secured to the plates 236, 238 the carriage member 240 may be positioned and locked in position relative to the board to provide some traction for the patient and thus relieve a degree of stress from the spine of the patient.

By providing the removable carriage member 240 the foot support 34 may be located to suit patients of different sizes. If a very short patient or a child is placed on the board, the carriage member 240 may also be removed from the trough 242 and reversed such that the foot support may be used by a patient whose feet only extend to the top of the trough. It will be noted that, in this particular configuration, the longitudinal foot plate 238 will not be available for supporting the feet of the patient.

Figure 16:
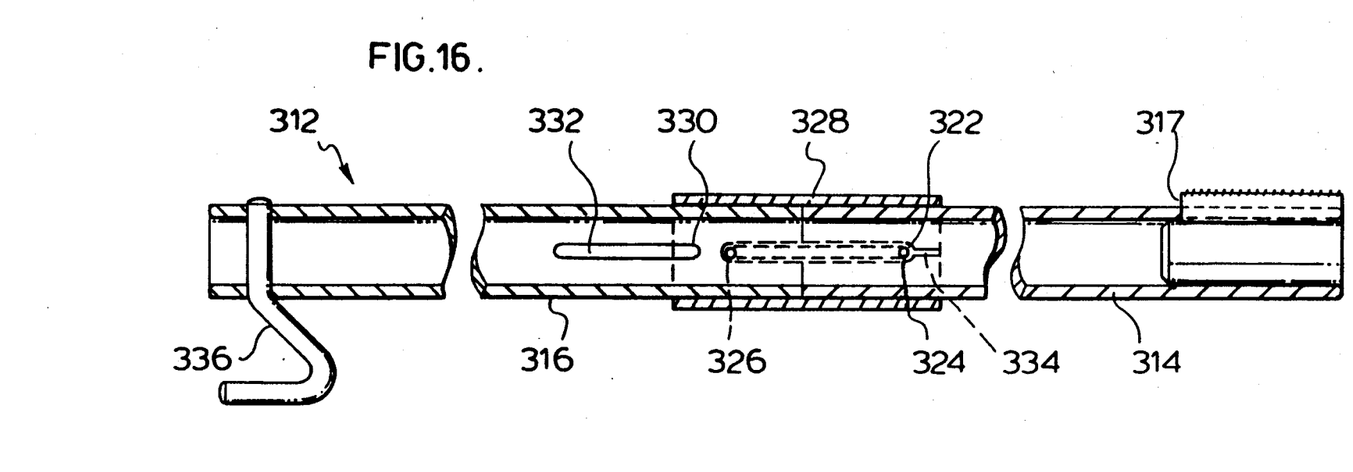
FIG. 16 is a sectional view of a bottle supporting post of the spinal restraint of FIG. 1.

The restraint is preferably further provided with provision for holding a bottle for use in the intravenous supply of fluid to the patient and a preferred arrangement is illustrated in FIG. 1. A bottle or other suitable container 310 is shown suspended from a post 312 mounted at the head of the restraint 20. Details of the post 312 and the mounting for the post are shown in greater detail in FIGS. 16 and 17 of the drawings, FIG. 16 showing a sectional view of the post 312, and FIG.

Figure 17:
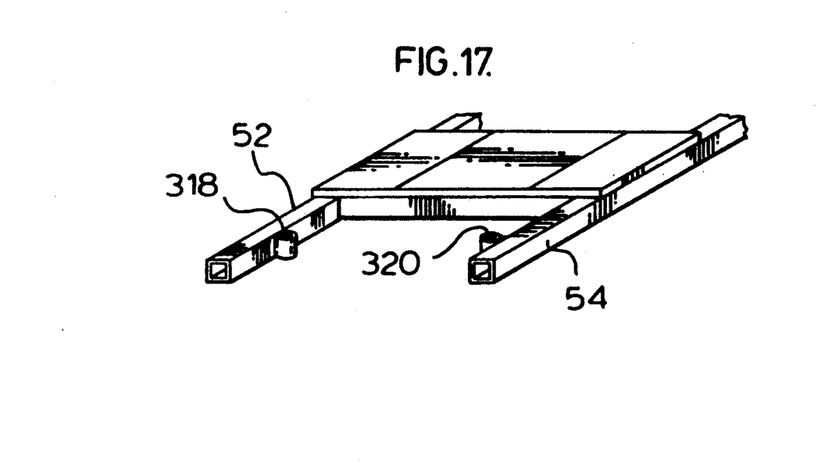
FIG. 17 is a simplified perspective view of the head of the spinal restraint of FIG. 1.

17 showing a simplified view of the head of the restraint 20.

To facilitate storage, the post 312 is formed of two hollow cylindrical parts 314, 316 which may be broken for convenient storage, as will be described. The lower part 314 is provided with a longitudinal slot 317 at the lower end thereof, for engaging one of a pair of keyhole shaped bosses 318, 320 fixed to inner faces of the frame side members 52, 54, which permits the post 312 to be mounted on either side of the restraint 20. The upper end of the lower part 314 is joined to the lower end of the upper part 316 by means of an internally mounted spring 322, extending between mounting pins 324, 326.

A cylindrical, tubular web 328 is mounted on the lower end of the upper part 316 and is provided with a radially, inwardly extending pin 330 for slidably engaging a slot 332 provided in the wall of the part 316. The web 328 is shown in a locking position in FIG. 16, with the web receiving the upper end of the lower part 314. To break the post 312, the web is slid upwardly until it clears the end of the part 314. To lock the parts 314, 316 against rotation, the lower end of the web 328 is provided with an open ended slot 334 for engaging the head of the spring mounting pin 324.

A hook 336 is provided at the upper end of the upper part 316 and may rotate relative to the post 312 so that the bottle 310 remains upright as the restraint 20 is tilted as it is carried.

Figure 18:
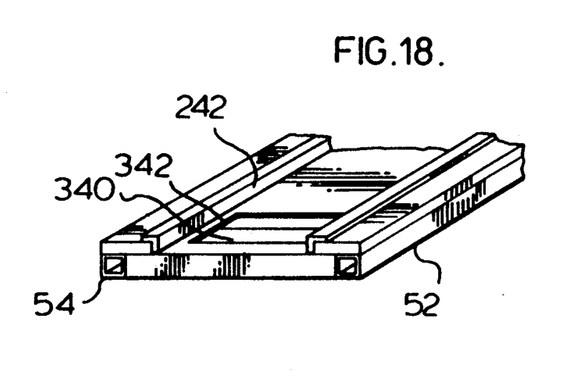
FIG. 18 is a simplified perspective view of the foot of the spinal restraint of FIG. 1.

For storage of the post 312, and of other "loose" items, a storage compartment 340 is provided between the base of the trough 242 and the rear cover of the restraint. The compartment is illustrated in FIG. 2 and also in FIG. 18 of the drawings. Access to the compartment 340 is gained through an opening 342 in the base of the trough 242, which may be covered by the carriage member 240 of the foot support 34.

It may be seen that the spinal restraint provides means for easily and securely immobilizing a patient having a suspect spinal injury. The longitudinally and laterally adjustable straps allow emergency personnel to quickly and easily secure a patient to the board. The head support permits the head of a patient to be held securely relative to the board and in the storage configuration allows the board to be slid beneath a patient and also permits compact storage of the restraint. In the support configuration, the foot support is easily adjustable to suit patients of all sizes and is configured to permit traction to be applied to the spine of the patient In the storage configuration, the foot support, like the head support, may be folded flat to facilitate storage of the restraint. The provision of carrying handles at the ends of the boards also permit easier carrying of the restraint by two bearers and facilitates the carrying of the restraint through narrow openings.

In summary, the spinal restraint, according to the present invention, provides apparatus for restraining a patient which is relatively easy to use, requires a minimum of separate parts for operation and which can be configured to a compact arrangement to facilitate storage on emergency response vehicles and the like.

We claim:
1. Apparatus for restraining a patient comprising:
   (A) a rigid board; and
   (B) A head support for immobilizing the head of a patient on the board comprising:
      (i) a centre support for supporting the back of the head of a patient;
      (ii) two side supports, one on either side of the central support, each one for supporting a side of the head of a patient, characterized in that:
         (a) each side support is pivotally mounted to the board about an axis substantially parallel to the longitudinal axis of the board for movement between a support configuration and a loading and storage configuration in which the side supports lie substantially flush with the centre support;
         (b) each side support is substantially rigid and laterally moveable to accommodate heads of different sizes;
         (c) each side support may be moved up and down relative to the board while in the support configuration;
         (d) each side support comprises a mounting member and a support member, the mounting member defining a track extending perpendicularly to the longitudinal axis of the board and the support member includes a track engaging portion; and
         (e) the mounting member is pivotally mounted to a carriage member, the carriage member being mounted on laterally extending track means provided on the board; and
      (iii) lock means for locking each side support in the support configuration.

2. The apparatus of claim 1 further comprising:
a plurality of retaining straps for extending laterally across the board from side portions thereof to secure a patient thereto,
characterized in that at least one of the straps is longitudinally adjustable to accommodate patients of different sizes.

3. The apparatus of claim 1 further comprising:
a plurality of retaining straps for extending laterally across the board from side portions thereof to secure a patient thereto,
characterized in that at least one of the straps is longitudinally adjustable and is laterally retractable to accommodate patients of different sizes.

4. The apparatus of claim 3, wherein releasable first locking means is provided to lock said at least one strap against lateral extension and retraction.

5. The apparatus of claim 4, wherein resilient strap retraction means is provided on the underside of the board and tends to retract said at least one strap.

6. The apparatus of claim 5, wherein said first locking means is in the form of a first locking buckle including a locking member and a locking surface, said at least one strap passing between the locking member and the locking surface, and the locking member being operable to engage a portion of said at least one strap between the locking member and locking surface.

7. The apparatus of claim 6, wherein said first locking means is located at a first side portion of the board and said resilient strap retraction means extends from a second side portion of the board and is attached to a portion of said at least one strap.

8. The apparatus of claim 7, wherein said resilient strap retraction means is attached to said at least one strap through a strap pulley located on a bight in the pulley, a first reach extending from the pulley and being fixed to said first locking buckle and a second reach extending from the pulley and passing between said locking member and said locking surface.

9. The apparatus of claim 8, wherein said resilient strap retraction means is in the form of a resilient loop passing around two longitudinally spaced pulleys mounted to the board, the strap pulley mounted to one reach of the loop.

10. The apparatus of claim 8, wherein said resilient strap retraction means is in the form of a resilient elongate member fixed between two fixed points on the board, the strap pulley being mounted to a mid-point of the member.

11. The apparatus of claim 2 or 3, wherein releasable first locking means is provided to lock said at least one strap against longitudinal movement.

12. The apparatus of claim 11, wherein said releasable first locking means is provided at a first side portion of the board, and first slidable mounting means are provided at a second side portion of the board.

13. The apparatus of claim 12, wherein said releasable locking means comprises a first locking buckle mounted on a first longitudinally extending track.

14. The apparatus of claim 13, wherein said first locking buckle includes a locking member and said first longitudinally extending track includes a locking surface, said locking member being operable for movement between an unlocked position and a locked position in which the locking member is in locking engagement with the locking surface.

15. The apparatus of claim 14, wherein said at least one strap passes between the locking member and the locking surface.

16. The apparatus of claim 15, wherein said first locking buckle includes track follower means for retaining the buckle on the track.

17. The apparatus of claim 16, wherein said track follower means engages surfaces of said track, said surfaces being oppositely directed to said locking surface.

18. The apparatus of claim 17, wherein said first locking buckle includes a mounting member, said locking member being mounted on said mounting member, and said track follower means being provided on said mounting member in the form of a pair of undercut slots formed in side portions thereof.

19. The apparatus of claim 18, wherein said locking member is mounted to a central portion of said mounting member, cam means being provided for movement of said locking member between the locked and unlocked configuration.

20. The apparatus of claim 19, wherein said locking member is pivotable on the mounting member about a first axis and said cam means is in the form of an operating member mounted on said mounting member and pivotable thereon about a second axis, a first portion of the operating member being located between the mounting member and the locking member and being movable to space the locking member from the mounting member and thus push the locking member into contact with locking surface.

21. The apparatus of claim 19, wherein a second portion of the operating member extends into a slot below the upper surface of the board and inwardly of the side of the board.

22. The apparatus of claim 20, wherein resilient strap retraction means is provided on the underside of the board and tends to retract said at least one strap.

23. The apparatus of claim 21, wherein said resilient strap retraction means extends from a second side portion of the board and is attached to a portion of said at least one strap.

24. The apparatus of claim 22, wherein said resilient strap retraction means is attached to said at least one strap through a strap pulley located on a bight in the pulley, a first reach extending from the pulley and being fixed to said first locking buckle and a second reach extending from the pulley and passing between said locking member and said locking surface.

25. The apparatus of claim 22, wherein said resilient strap retraction means is in the form of one of a resilient loop passing around two longitudinally spaced pulleys mounted to the board, the strap pulley mounted to one each of the loop and a resilient elongated member fixed between two fixed points on the board, the strap pulley being mounted to a mid point of the member.

26. The apparatus of claim 22, wherein three retaining straps are provided, a first strap to secure the chest of a patient, a second strap to secure the pelvic area of a patient, and a third strap to secure the legs of a patient.

27. The apparatus of claim 26, wherein each strap is in two parts, one part extending from a respective side of the board, and the ends of the parts being provided with releasable engagement means to releasably join the ends.

28. The apparatus of claim 27, wherein one part of the strap extends from the locking means on one side of the board and the other part extends from a mounting means slidably mounted on a longitudinal track on the other side of the board.

29. The apparatus of claim 28, wherein the board includes recesses for accommodating the engagement means when the board is not in use.

30. The apparatus of claim 1, wherein lock means are provided for locking each support member in position on the mounting member relative to the board.

31. The apparatus of claim 30, wherein the lock means are each in the form of screw clamp mounted on the support member for engaging the mounting member.

32. The apparatus of claim 31, wherein lock means are provided for locking each carriage member relative to the board.

33. The apparatus of claim 32, wherein the lock means for locking each side support in the support configuration is in the form of a pivoted link extending between the carriage member and the mounting member.

34. The apparatus of claim 33, wherein inflatable air cushions are provided on the supports.

35. The apparatus of claim 34, wherein pump means are provided for inflating the air cushions.

36. The apparatus of claim 35, wherein the pump means include a valve means which opens when the pressure in the air cushions exceeds a predetermined level.

37. The apparatus of claim 1, wherein a strap is provided to extend between the side supports and retain the head of a patient against the centre support.

38. The apparatus of claim 1 further comprising:
body retaining means for securing a patient to the board; and
a foot support for supporting the feet of a patient and extending from the board,
characterized in that the foot support is mounted on carriage means adapted for engaging track means extending longitudinally of the board, the carriage means including locking means for locking the carriage means, and the foot support, at selected locations on the board to accommodate patients of different sizes.

39. The apparatus of claim 38, wherein foot retaining means are provided for securing the feet of a patient to the foot support.

40. The apparatus of claim 39, wherein the foot support includes a first foot support member moveable between a support configuration in which the member extends laterally of the board and is substantially perpendicular to the board surface and a storage configuration in which an upper surface of the member lies substantially parallel to and adjacent the board surface.

41. The apparatus of claim 40, wherein the foot support includes a second foot support member for location between the feet of a patient to provide lateral support.

42. The apparatus of claim 41, wherein the second foot support is mounted on the carriage means and is moveable between a support configuration, in which the second foot support member extends longitudinally of the board and perpendicular to the board surface and the first foot support member, and a storage configuration in which the member lies parallel to and adjacent the board surface.

43. The apparatus of claim 42, wherein the first foot support member is pivotable relative to the carriage means about axis which extends laterally of the board and the second foot support member is pivotable relative to the carriage means about an axis which extends longitudinally of the board.

44. The apparatus of claim 43, wherein the carriage means is removable from the track means and may be mounted to the track means in two configurations, in the first configuration with the second foot support member located on the side of the first foot support member for abutting the feet of a patient, and in the second configuration with the second foot support member on the opposite side of the first foot support member for abutting the feet of a patient to accommodate smaller patients.

45. The apparatus of claim 44, wherein the first and second foot support members are in the form of first and second foot plates.

46. The apparatus of claim 45, wherein the foot retaining means is in the form of a strap for securing the feet of a patient to the first foot plate.

47. The apparatus of claim 46, wherein the first foot plate has sides, the base of each side including a strap retaining portion.

48. The apparatus of claim 47, wherein each strap retaining portion is in the form of an open slot formed in the first foot plate.

49. The apparatus of claim 48, wherein the second foot plate includes a strap retaining portion for engaging a centre part of the strap extending over the feet of a patient.

50. The apparatus of claim 49, wherein the strap retaining portion is in the form of a slot provided in the second foot plate.

51. The apparatus of claim 50, wherein a plurality of longitudinally spaced slots are provided in the second foot plate.

52. The apparatus of claim 51, wherein the slots are formed as a comb.

53. The apparatus of claim 45, wherein the carriage means is formed of a thin, planar carriage member and the track means is in the form of a shallow trough in the surface of the board, carriage lock members being provided at the sides of the carriage member for releasably engaging sides of the trough.

54. The apparatus of claim 53, wherein the carriage lock members include teeth adapted for engaging corresponding longitudinally spaced recesses provided in the sides of the trough.

55. The apparatus of claim 54, wherein the carriage lock members are laterally movable by means of a longitudinally moveable operating member, co-operating cam surfaces being provided on the carriage lock members and operating member.

56. The apparatus of claim 55, wherein the carriage lock members are located at one end of the carriage member and the operating member extends from the other end of the carriage member.

57. The apparatus of claim 56, wherein means are provided on the carriage member for releasably retaining the operating member in the locking position.

58. The apparatus of claim 45, wherein the first and second foot plates include releasable interengaging lock means for locking the plates to one another in the support configurations.

59. The apparatus of claim 58, wherein the first foot plate is provided with an aperture for receiving a locking portion of the second foot plate, said locking portion including an aperture for engaging a latch member provided on the first foot plate.

60. The apparatus of claim 1 further comprising:
body retaining means for securing a patient to the board; and
handle means for carrying the board,
characterized in that the handle means are located at ends of the board and are movable between a carrying configuration in which the handle means extend beyond the ends of the board, and a storage configuration which the handle means are located substantially adjacent the ends of the board.

61. The apparatus of claim 60, wherein the handle means is in the form of two U-shaped handle members having side portions and a cross portion, one handle member being provided at each end of the board and the board having channels for slidably receiving said side portions.

62. The apparatus of claim 1 further comprising:
a plurality of retaining straps for extending laterally across the board from side portions thereof to secure a patient thereto,
characterized in that at least one of the straps is laterally retractable to accommodate patients of different sizes.

63. Apparatus for restraining a patient comprising;
a rigid board;
a plurality of retaining straps for extending laterally across the board from side portions thereof, the straps being longitudinally adjustable and laterally retractable;
a head support for immobilizing the head of a patient on the board, and comprising a centre support for supporting the back of the head of a patient and two side supports, one on either side of the central support, each one for supporting the side of the head of a patient and being moveable between a support configuration and a loading and storage configuration in which the side supports lie substantially flush with the centre support;
a foot support for supporting the feet of a patient and extending from the board in a support configuration and moveable to a storage configuration in which the foot support lies substantially flush with the board, the foot support being mounted on carriage means adapted for engaging track means extending longitudinally of the board, the carriage means including locking means for locking the carriage means, and the foot support, at selected locations on the board; and handle means for carrying the board located at ends of the board and being moveable between a carrying configuration in which the handle means extend beyond the ends of the board, and a storage configuration in which the handle means are located substantially adjacent the ends of the board.

64. The apparatus of claim 63, and further comprising an intravenous supply mounting post, mounting means being provided on the board for removably mounting the post.

65. The apparatus of claim 63, wherein a storage compartment is provided in the board having an access opening which may be closed by the carriage member of the foot support.

* * * * *